(12) United States Patent
Lee

(10) Patent No.: US 8,029,480 B2
(45) Date of Patent: Oct. 4, 2011

(54) INJECTION-VOLUME REGULATING DEVICE OF LIQUID MEDICINE

(75) Inventor: Sang-Bin Lee, Seoul (KR)

(73) Assignee: Meinntech Co., Ltd., Anyang (KR)

( * ) Notice: Subject to any disclaimer, the term of this patent is extended or adjusted under 35 U.S.C. 154(b) by 1147 days.

(21) Appl. No.: 11/632,290

(22) PCT Filed: Jul. 14, 2005

(86) PCT No.: PCT/KR2005/002270
§ 371 (c)(1),
(2), (4) Date: Jun. 11, 2007

(87) PCT Pub. No.: WO2006/009369
PCT Pub. Date: Jan. 26, 2006

(65) Prior Publication Data
US 2007/0293828 A1 Dec. 20, 2007

(30) Foreign Application Priority Data
Jul. 16, 2004 (KR) .................. 10-2004-0055659

(51) Int. Cl.
*A61M 5/00* (2006.01)
*F16L 37/28* (2006.01)
(52) U.S. Cl. ..................... 604/246; 251/149.5
(58) Field of Classification Search .......... 604/251, 604/246, 30, 32, 118, 186, 348, 252–255; 251/149, 149.5, 160
See application file for complete search history.

(56) References Cited

U.S. PATENT DOCUMENTS

| 4,515,588 | A | * | 5/1985 | Amendolia | 604/118 |
| 4,769,012 | A | * | 9/1988 | Quang et al. | 604/247 |
| 4,802,506 | A | * | 2/1989 | Aslanian | 137/556 |
| 5,005,604 | A | * | 4/1991 | Aslanian | 137/556 |
| 5,009,251 | A | * | 4/1991 | Pike et al. | 137/599.06 |
| 5,113,904 | A | * | 5/1992 | Aslanian | 137/556 |
| 5,234,413 | A | * | 8/1993 | Wonder et al. | 604/248 |
| 5,240,035 | A | * | 8/1993 | Aslanian et al. | 137/501 |
| 6,195,012 | B1 | * | 2/2001 | Yang | 340/618 |
| 6,213,986 | B1 | * | 4/2001 | Darling, Jr. | 604/248 |
| 6,916,010 | B2 | * | 7/2005 | Beck et al. | 251/209 |
| 6,921,389 | B2 | * | 7/2005 | Scagliarini et al. | 604/248 |
| 7,011,651 | B2 | * | 3/2006 | Lee et al. | 604/251 |

(Continued)

FOREIGN PATENT DOCUMENTS

| KR | 20-0265972 | 2/2002 |
| KR | 10-0472044 | 2/2005 |

*Primary Examiner* — Theodore Stigell
*Assistant Examiner* — Andrew Gilbert
(74) *Attorney, Agent, or Firm* — Greer, Burns & Crain, Ltd.

(57) ABSTRACT

An injection volume regulating device for liquid medicine, including a fixing member, a regulating member, a passage recess-sealing member, an outflow hole-sealing member, and a fastening member. The fixing member includes an inlet connected to a medicine supply hose, an inflow hole to deliver the medicine to the regulating device, an outflow hole to be supplied with the medicine from the regulating member, an outlet to discharge the medicine to the hose to allow the medicine to be supplied to a needle, and an insertion hole to be equipped with the fastening member. The regulating member includes a passage recess that is connected to the inflow hole, a liquid medicine-delivering groove connected to the outflow hole, and an insertion hole to be equipped with the fastening member. The passage recess-sealing member communicates the inflow hole with the passage recess. The fastening member fastens the fixing member to the regulating member.

18 Claims, 14 Drawing Sheets

U.S. PATENT DOCUMENTS 7,361,165 B2 * 4/2008 Simon .......................... 604/246
2003/0135164 A1 * 7/2003 Simon .......................... 604/246
2005/0065480 A1 * 3/2005 Lee et al. ...................... 604/246
2007/0293828 A1 * 12/2007 Lee .............................. 604/246

* cited by examiner

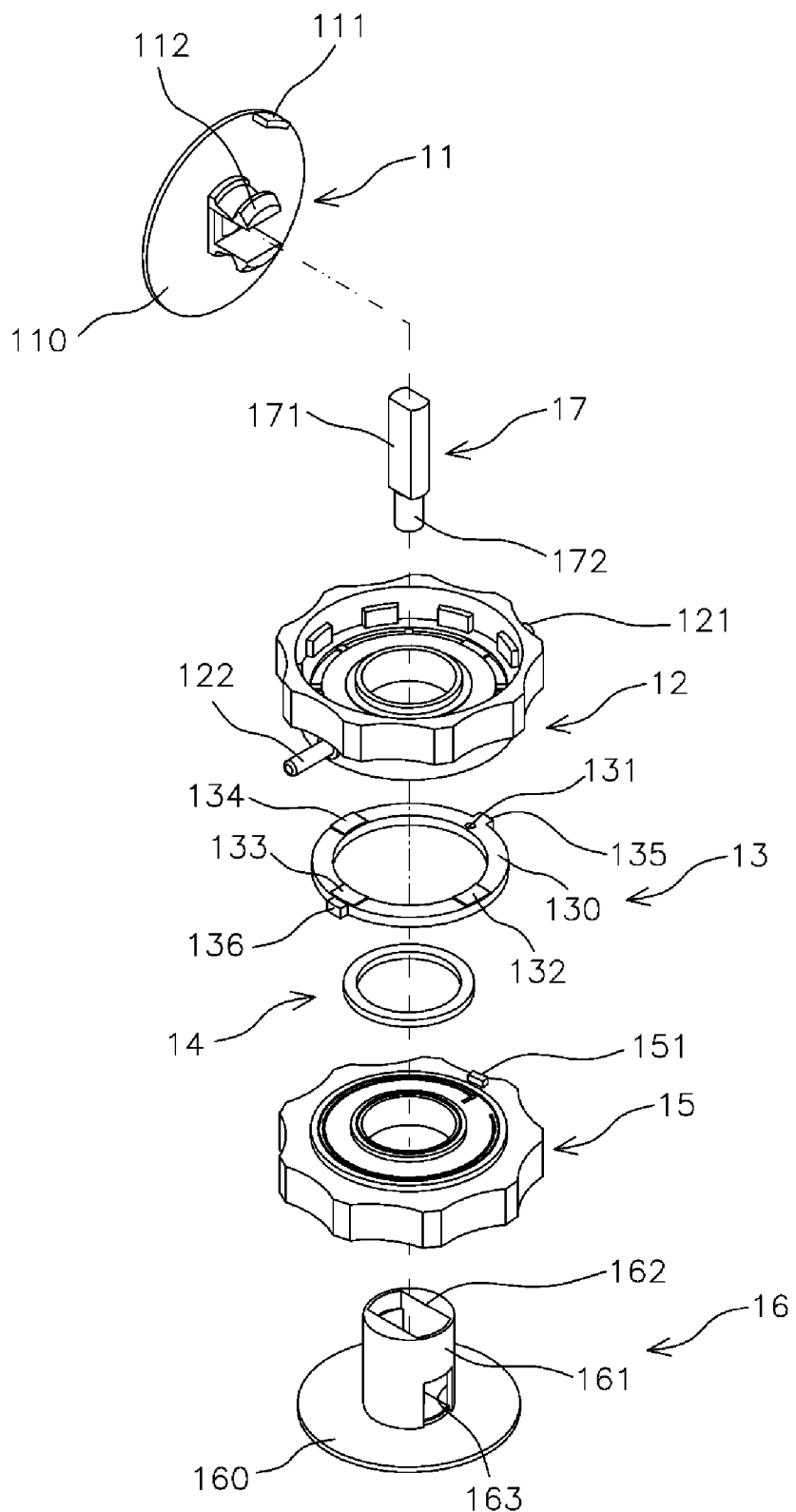
[Fig. 1]

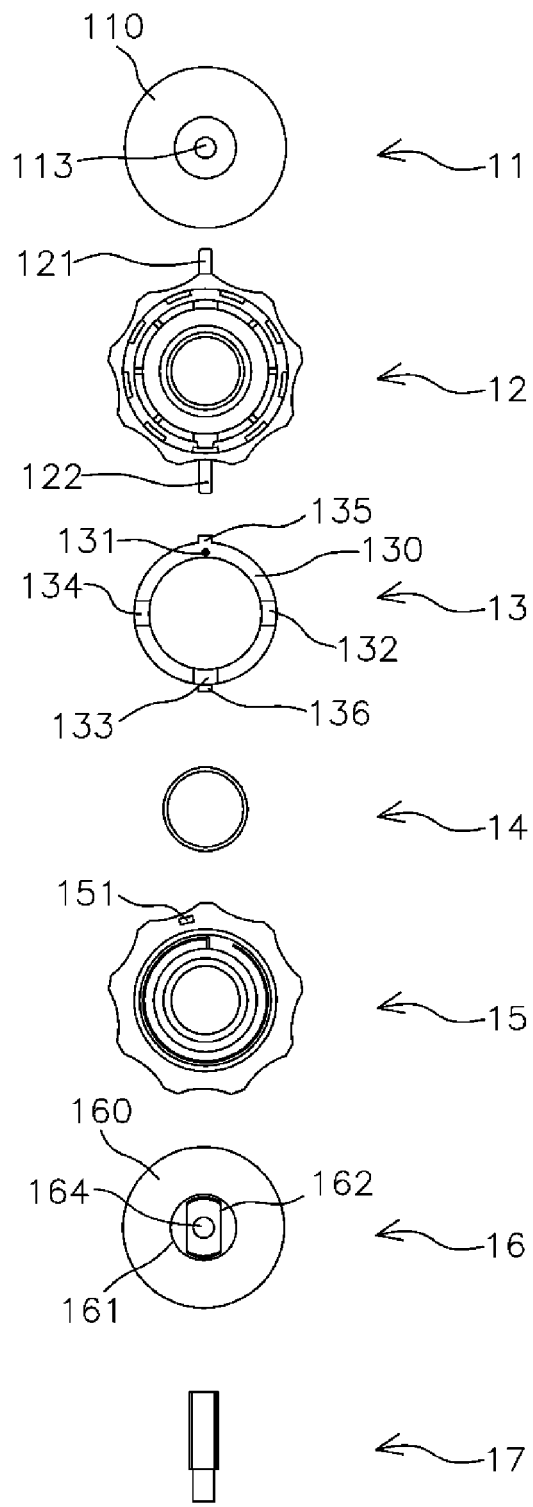
[Fig. 2]

[Fig. 3]
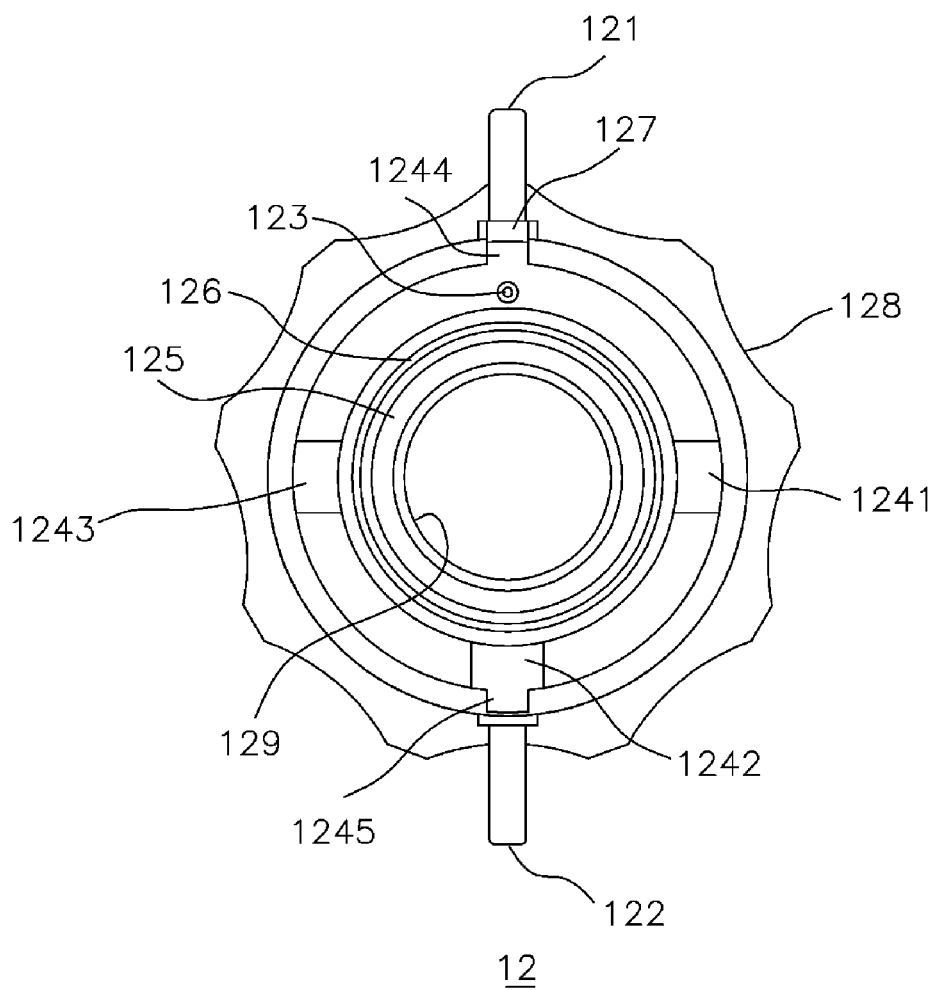
[Fig. 4]
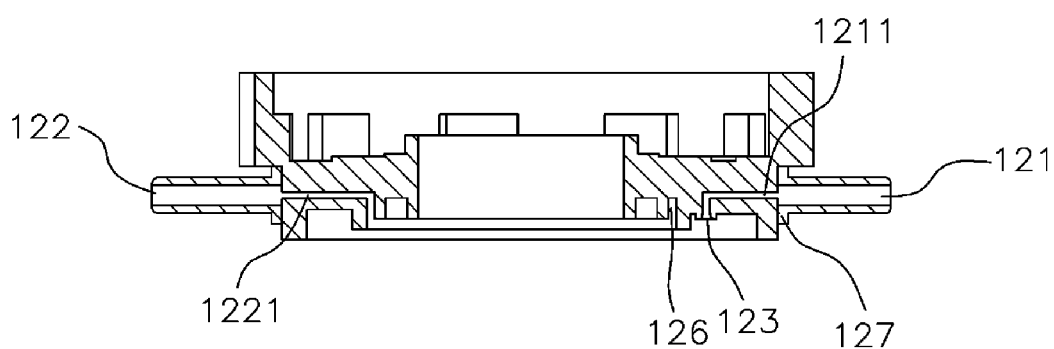

[Fig. 5]
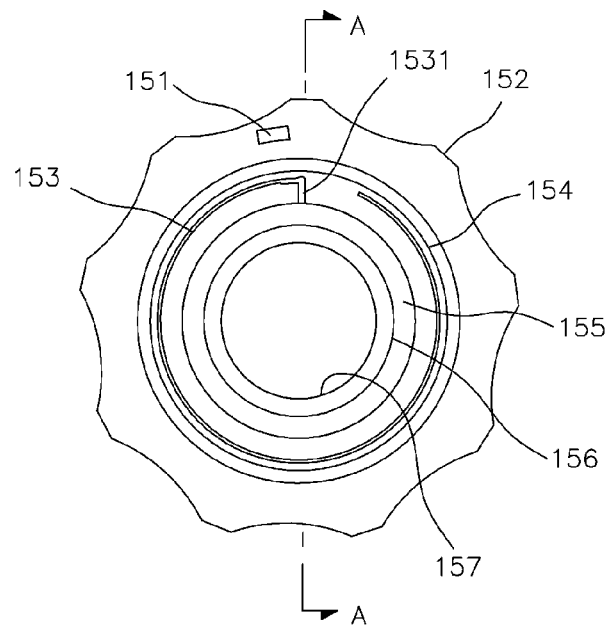
[Fig. 6]
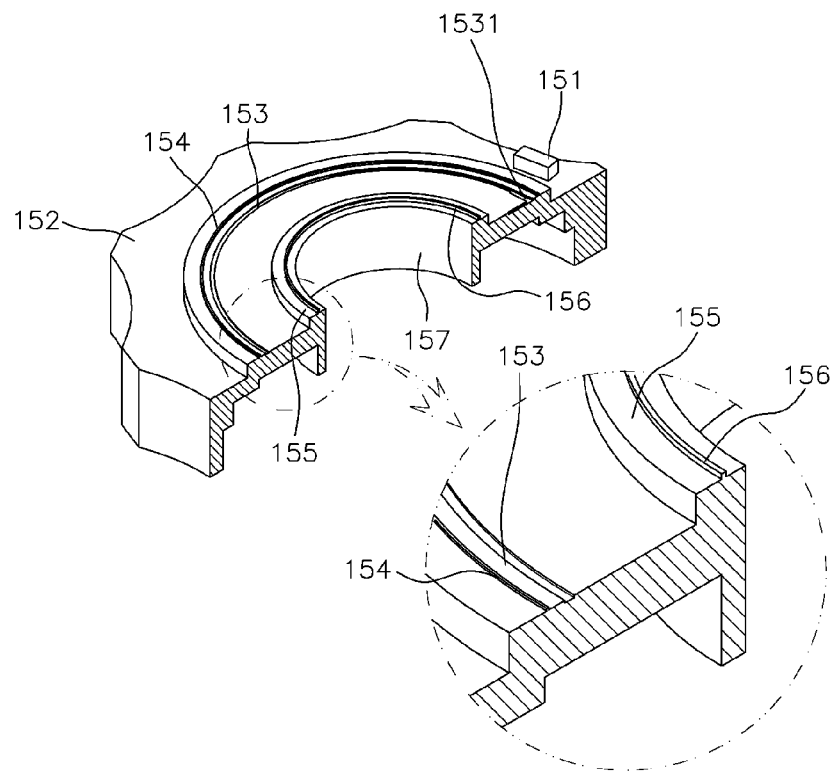

[Fig. 7]
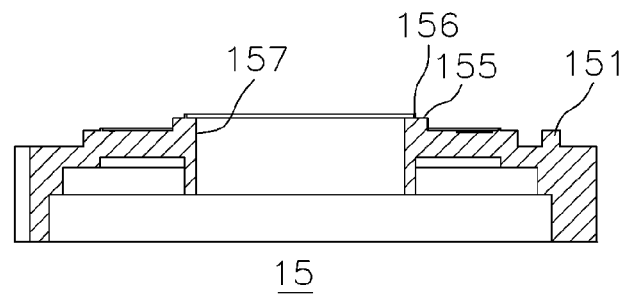
[Fig. 8]
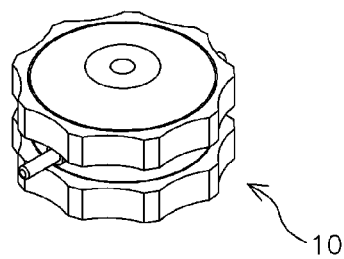
[Fig. 9]
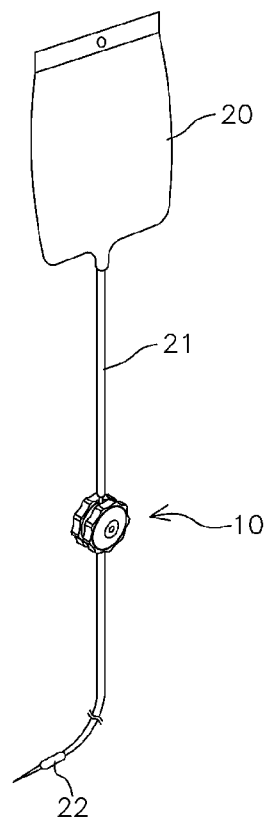

[Fig. 10]
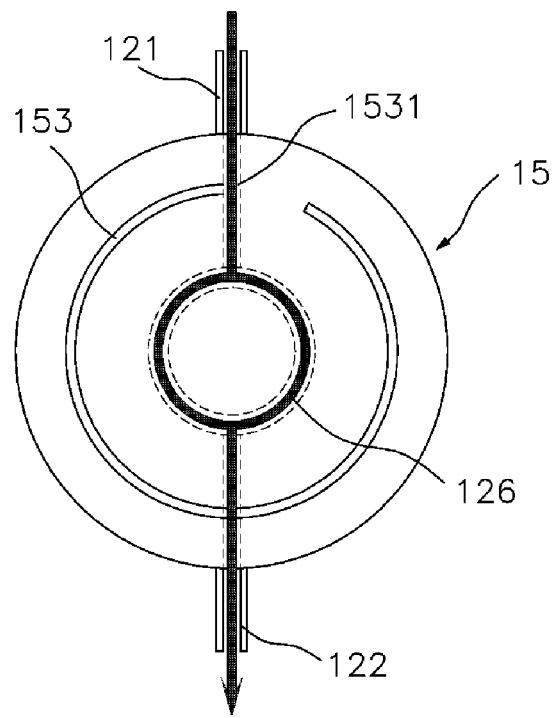
[Fig. 11]
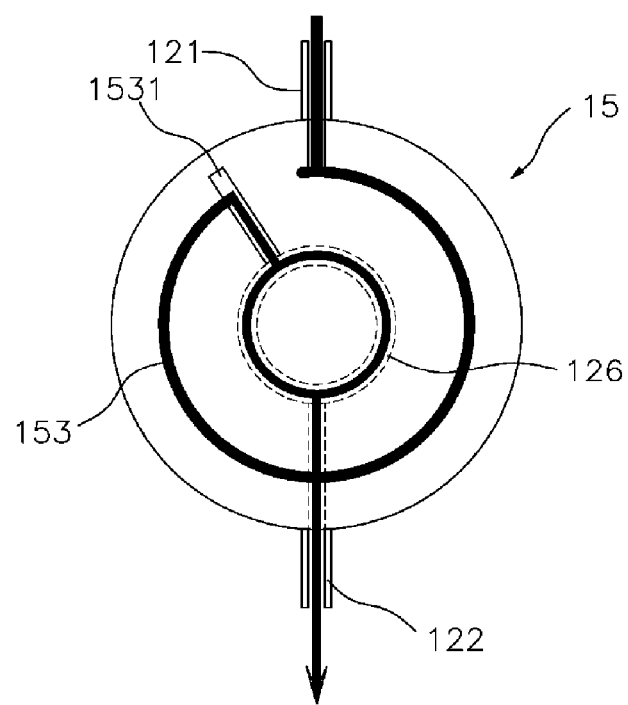

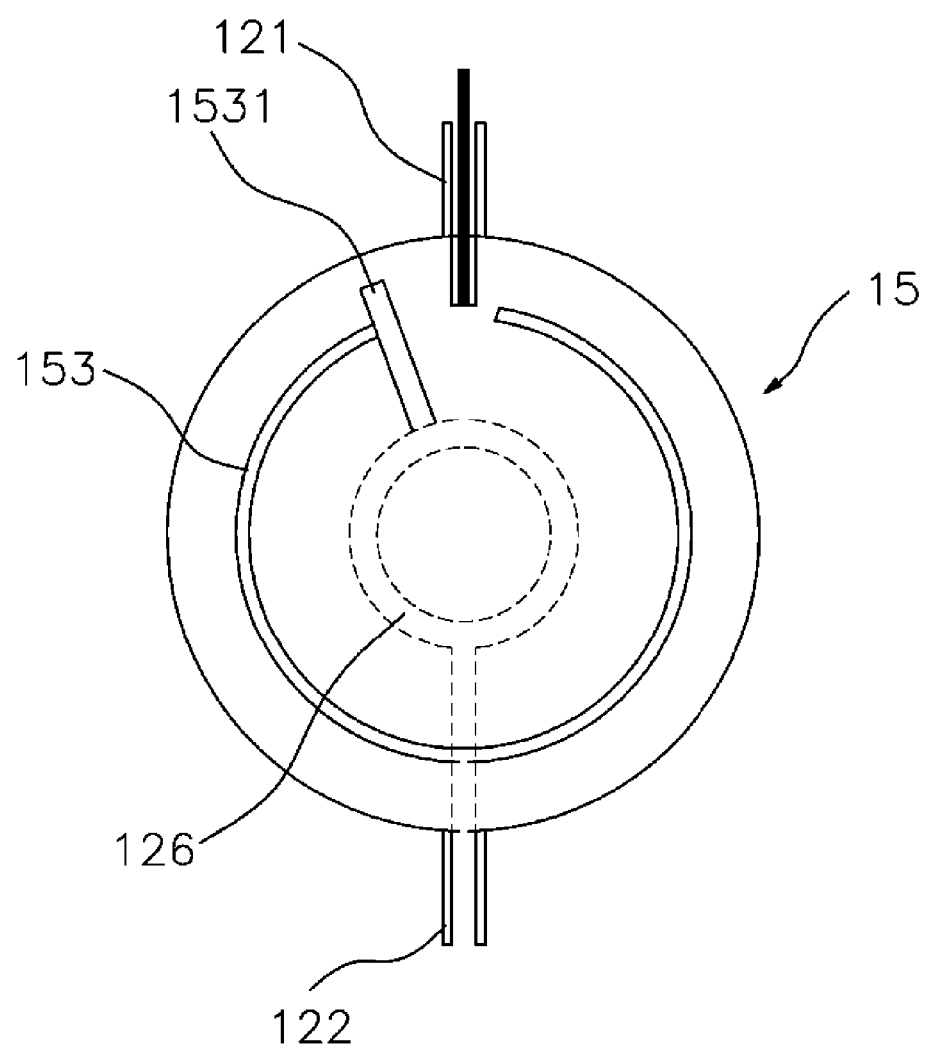
[Fig. 12]

[Fig. 13]
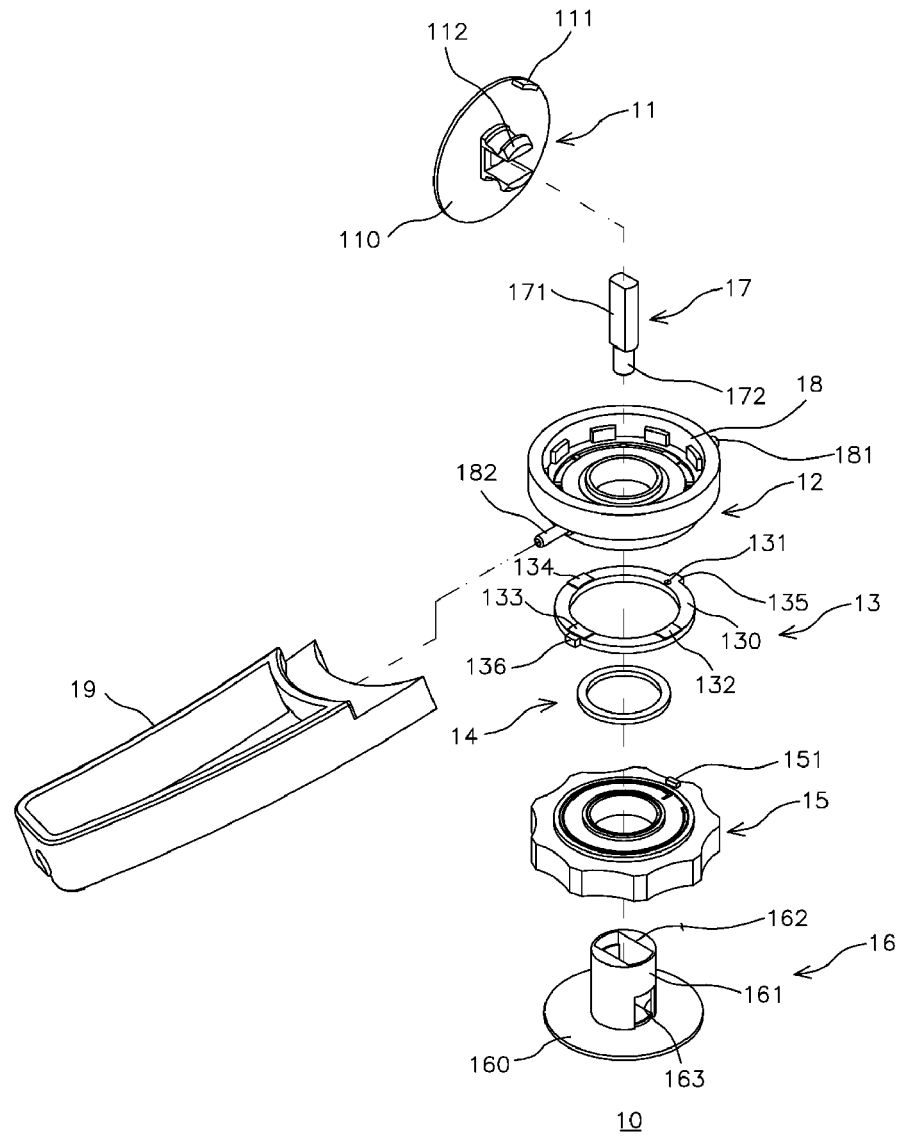
[Fig. 14]
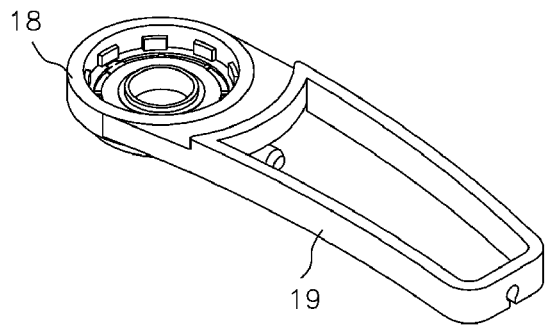

[Fig. 15]
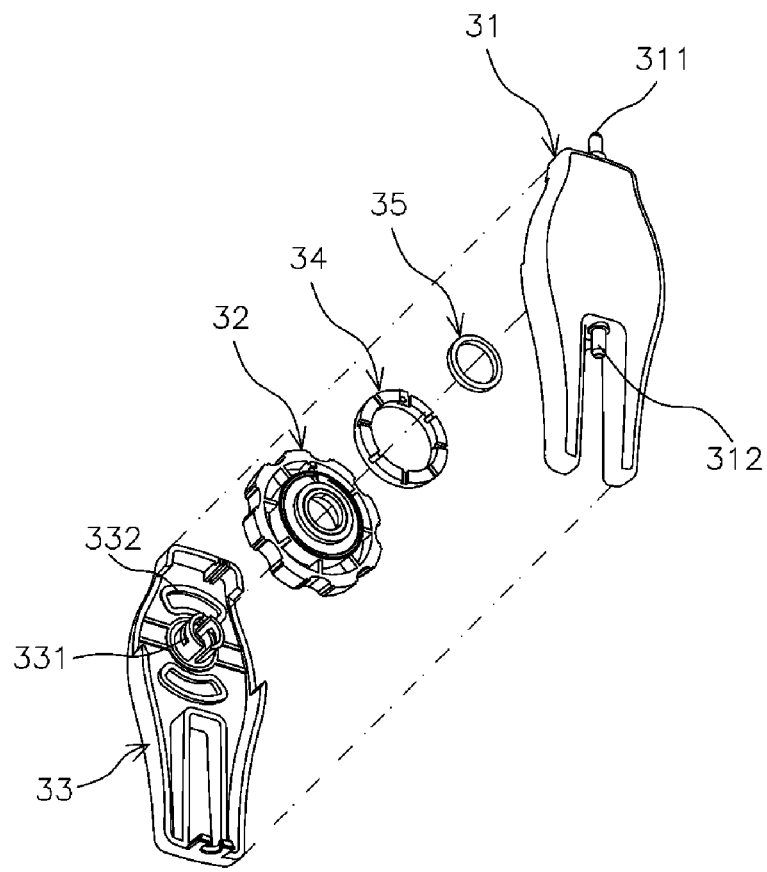
[Fig. 16]
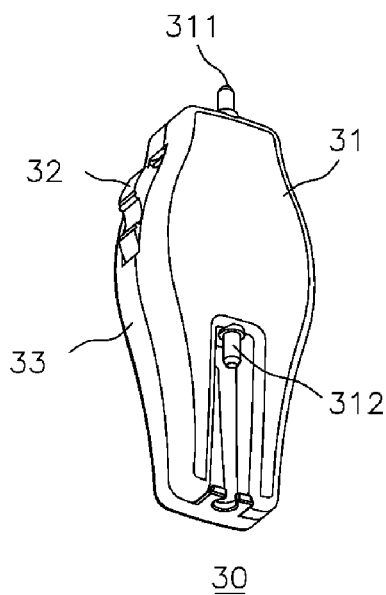

[Fig. 17]
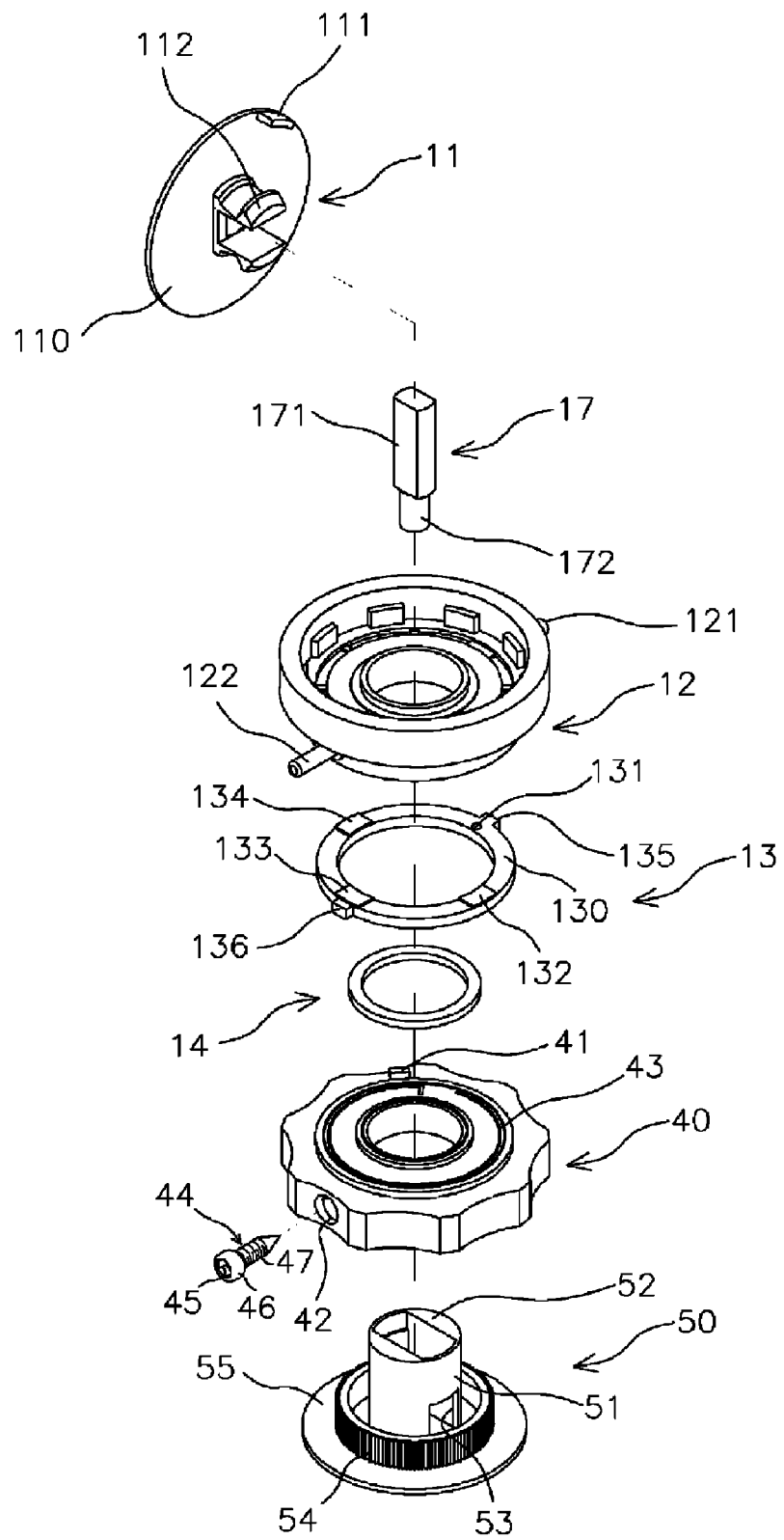

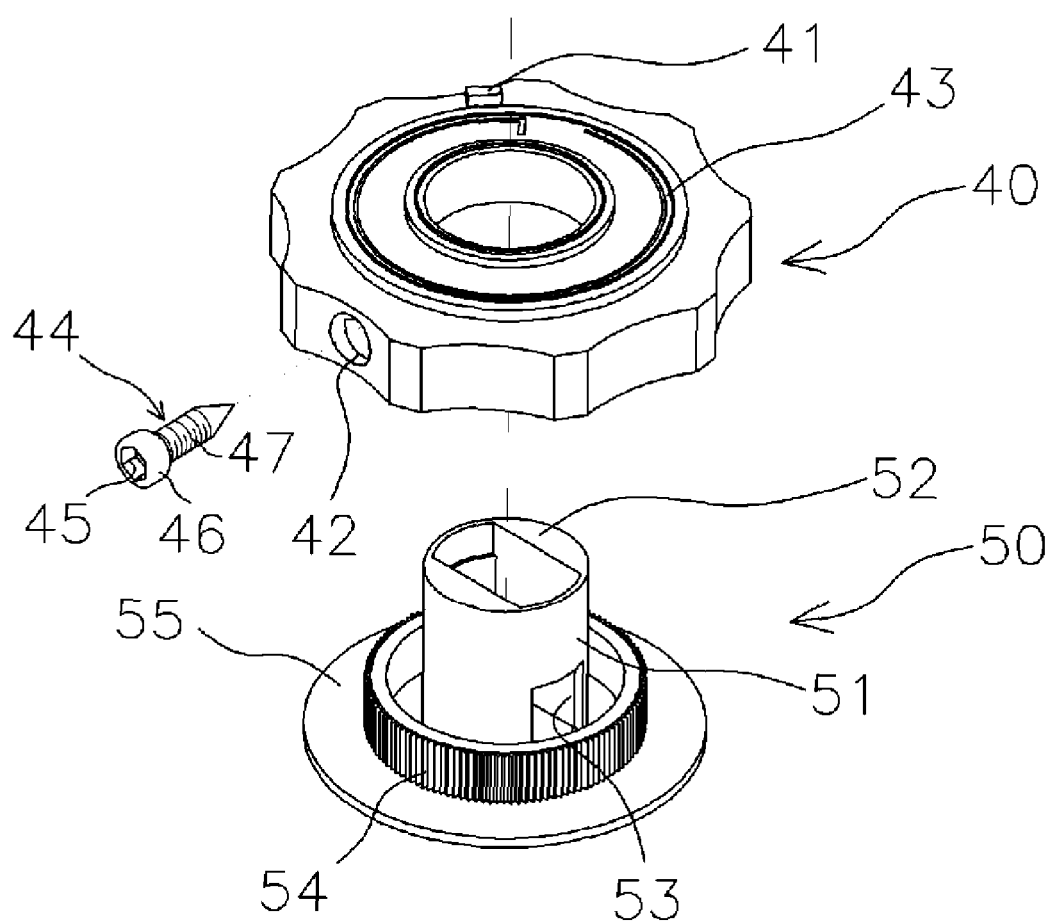
[Fig. 18]

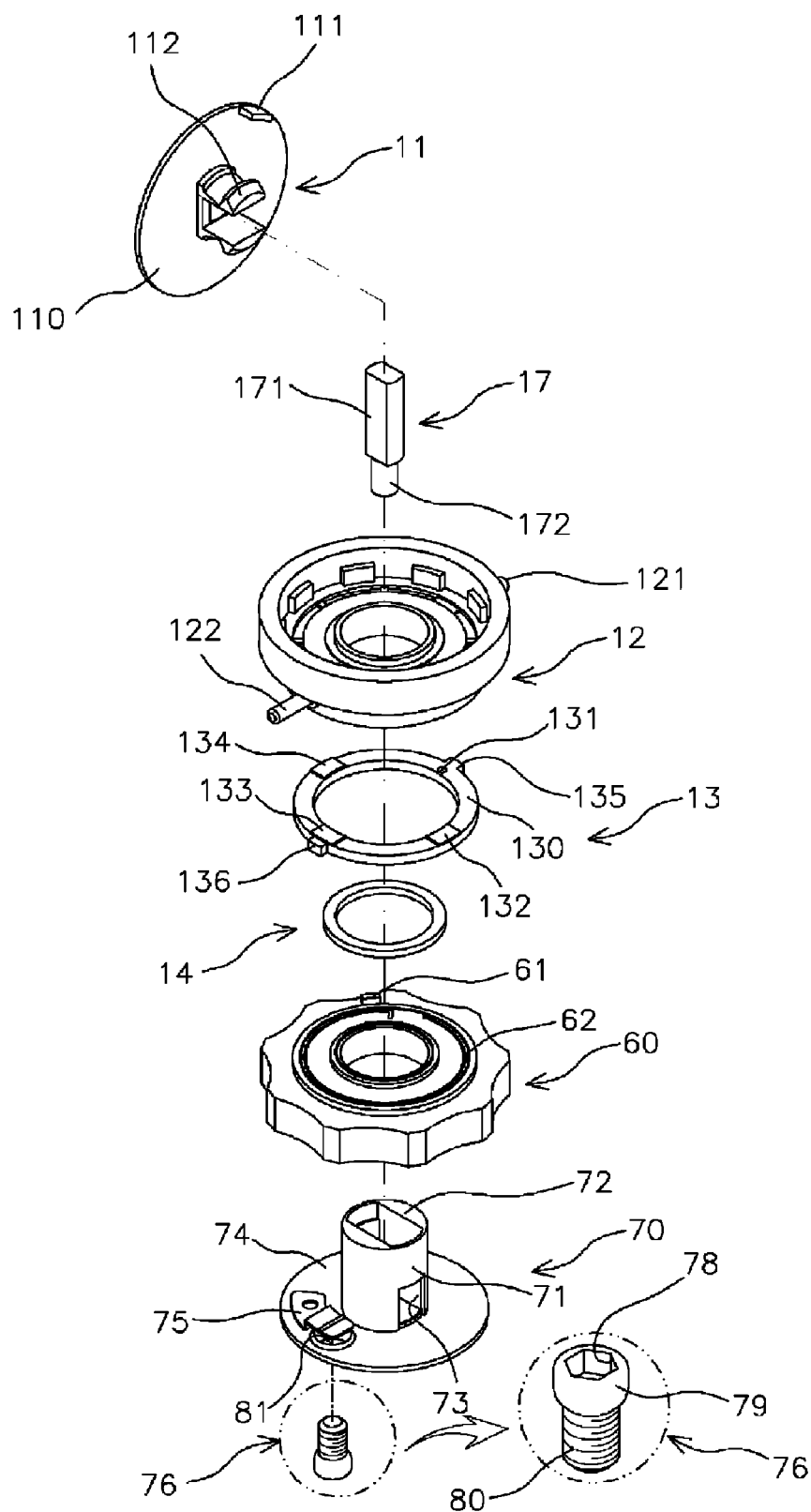
[Fig. 19]

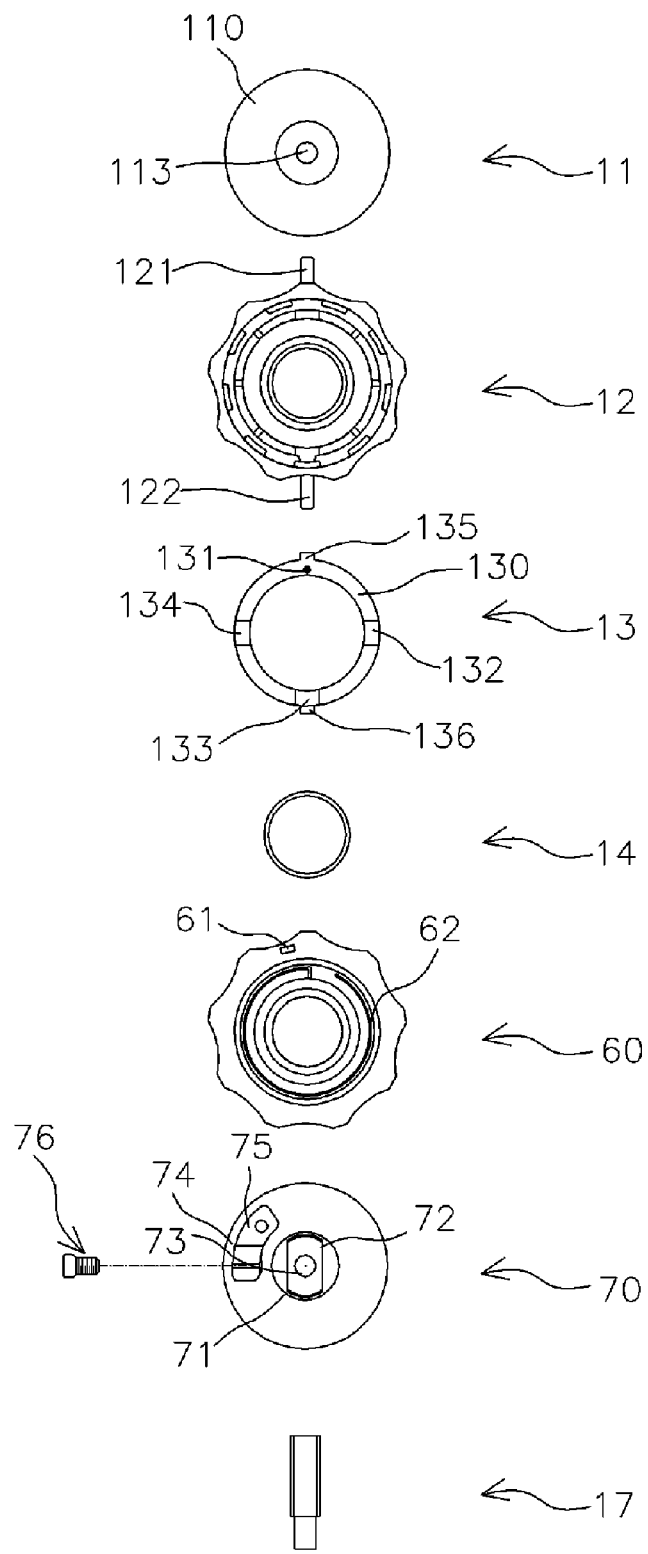
[Fig. 20]

[Fig. 21]
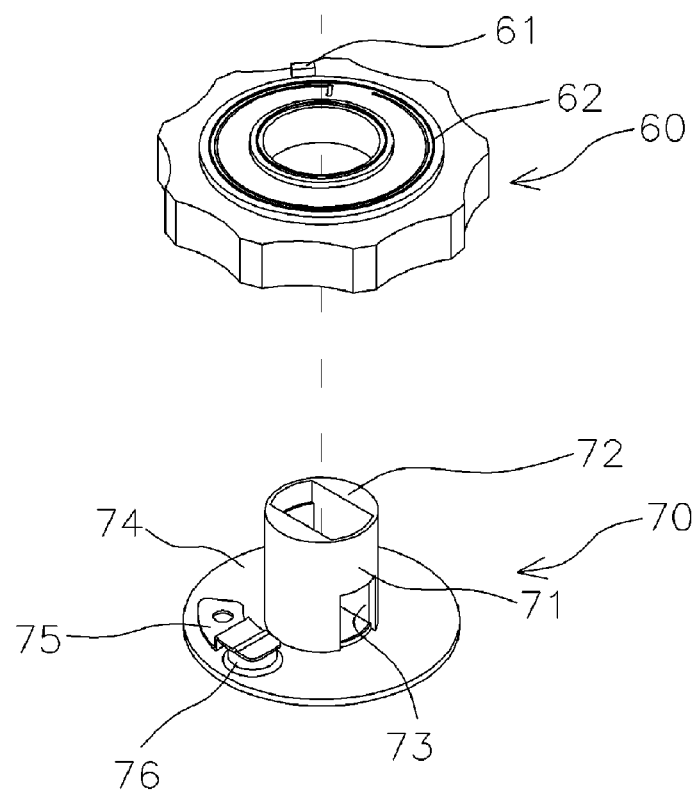
[Fig. 22]
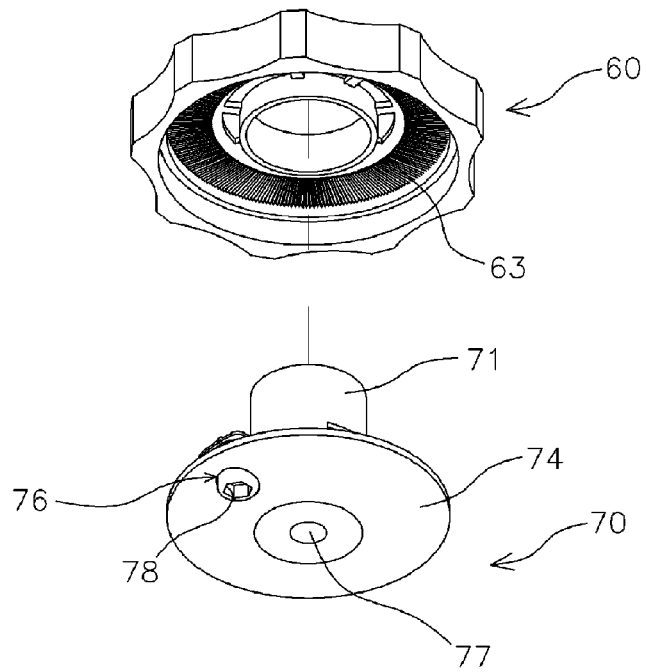

INJECTION-VOLUME REGULATING DEVICE OF LIQUID MEDICINE

TECHNICAL FIELD

The present invention relates to an injection volume regulating device for a liquid medicine, and more particularly to an injection volume regulating device for a liquid medicine, designed to allow a flow rate of the liquid medicine to be precisely adjusted through change in a length and a cross-sectional area of a passage through which the liquid medicine flows, to prevent a packing for sealing from infiltrating the passage and from being pushed by pressure buildup thereon, and to be operated with one hand.

BACKGROUND ART

In general, patients suffer from indigestion due to impaired function of the stomach and intestine, so that sufficient nutrition cannot be ensured with food alone. Thus, Ringers solution contained in a Ringer-pack is injected into a blood vessel of the patient to provide necessary nutrients, in particular, glucose, to the patient.

For oral medication, various products have been developed, which can maintain effects over 24 hours or more, but, in the case of injectable medicines, it is difficult to maintain effects for 24 hours. However, it is well known that, if the injectable medicine of a predetermined amount or more can be continuously administered at a constant rate for 24 hours or more, the injectable medicine can provide more constant effects than oral medication without side reactions.

In particular, for infants, an administration amount of a liquid medicine is determined in proportion to a weight of the infant patient (in other words, an injection amount of the liquid medicine is determined by multiplying an injection volume of the medicine per kg by the weight of the infant patient), and thus it is necessary to provide a device which can deliver the liquid medicine for a predetermined period of time through flexible adjustment in the injection amount of the liquid medicine.

Additionally, since infants frequently move about during administration, there is a problem in that, when the liquid medicine is administered using a conventional clamp, the clamp becomes loose due to movement of the infant patient, making it difficult to inject the liquid medicine in an exact amount.

Furthermore, when administrating a special liquid medicine for injection, such as anti-cancer agents, antibiotics and the like, to a patient in critical condition, the liquid medicine must be continuously administered at a constant rate in a suitable amount according to conditions of the critical patient.

If the suitable amount of the special liquid medicine for injection is not continuously administered at a constant rate to the patient, there is a high possibility of side reactions, such as anaphylactic shock.

Thus, it is necessary to provide an injection volume regulating device for a liquid medicine, which enables continuous injection of the liquid medicine at a constant rate into the blood vessel.

The conventional clamp can regulate the injection volume of the liquid medicine such that about 70~80 ▯/hr of liquid medicine is delivered therethrough. The conventional clamp is equipped to an outer portion of a hose which is hermetically connected to a lower end of a pack containing a liquid medicine and to a needle, and regulates the injection volume of the liquid medicine through change in cross-sectional area of the hose by compressing the hose.

Generally, the hose is compressed by a regulating member, which can move up and down along a tapered guider, and which comprises a roller typically having small teeth formed on an outer surface thereof. The guider is tapered such that, when the roller reaches one end of the guider, the roller compresses the hose, and when the roller reaches the other end, it completely opens the hose.

With this construction, the injection volume of the liquid medicine flowing in the needle is regulated by changing the cross-sectional area of the hose while rolling the regulating member up and down along the guider. However, with the conventional clamp, it is very difficult to accurately adjust a flux of the liquid medicine since the regulating member cannot tightly compress the hose when it is excessively used, and since the hose is composed of a synthetic resin or a rubber material.

Accordingly, during administration of the liquid medicine using the conventional clamp, changes in administration amount of the liquid medicine occur due to deformation of the regulating member as described above, requiring a nurse to frequently confirm the administration amount of the liquid medicine.

However, since the conventional clamp has advantages of a lower price and a simple construction, it is often used for the case where the liquid medicine is administered to a patient for a short period of time without high accuracy.

Although an infusion pump is known in the art as a device for precise regulation in infusion amount of a liquid medicine, the infusion pump is very expensive, resulting in heavy cost burdens to employ infusion pumps. In addition, a rechargeable electric device usually contained in the infusion pump may cause defective operation of the infusion pump, and large volume and heaviness of the infusion pump hinders portability.

However, it is necessary to use a device for precise regulation in pediatrics.

A flow controller is a disposable device for precisely regulating the injection volume of the liquid medicine, and can be used for the infant patient, an elderly patient, a patient suffering from adverse drug reaction, a patient requiring anti-cancer injection, and the like. The flow controller is inexpensive, and can replace the clamp and the infusion pump.

The flow controller ensures continuous administration of the liquid medicine at a constant rate for 24 hours or more after being set once, and is inexpensive in comparison to the infusion pump. The flow controller is highly portable, provides user convenience, and is applicable to all patients requiring injection. In addition, the flow controller reduces nurse workload and provides stability.

Various types of flow controller as described above have been developed, and generally have a spiral or arcuate shape.

However, the conventional flow controller has passages defining a plane perpendicular to an injecting direction of the liquid medicine, and two flat disks facing each other while being parallelly located at upper and lower portions, and an inlet and an outlet formed at the center of the disks, respectively.

As a result, it is difficult to manufacture the conventional flow controller and to operate the flow controller with one hand due to the complicate structure, such as two or more passages formed therein, increasing manufacturing costs.

In order to solve this problem, the applicant of the present invention invented a device, entitled Injection volume regulating device for liquid medicine, and filed it with Korean Industrial Property Office on Nov. 29, 2001 (Korean Patent Application No. 10-2001-0074845). The device comprises a regulating member, a fixing member, a rubber packing, and a fastening member. The invention of the disclosure is characterized in that the device has a single passage which is formed in a plane parallel to the injecting direction of the liquid medicine. The device comprises two flat disks, i.e. the fixing member and the regulating member, facing each other while being parallelly located at the right and left sides, and an inlet and an outlet formed at upper and lower portions of the fixing member.

The passage is formed in the device such that the liquid medicine enters the inlet of the fixing member, and passes through the passage formed in the regulating member, and is then discharged through the outlet of the fixing member. The passage has an arcuate shape with its central angle being about 350 degrees, and has a tapered cross-section.

However, the device of the disclosure has problems in that the rubber packing compresses the passage and interferes with flow of the liquid medicine, the fastening member is pushed by restoring force of the rubber packing, and in that the rubber packing is not fixed in the device.

Additionally, although it is needed to provide an injection volume regulating device for a liquid medicine which can be easily adjustable with one hand for enhancing operating efficiency of a user, a device completely solving the above described problems has yet to be developed.

DISCLOSURE OF INVENTION

Technical Problem

Therefore, the present invention has been made in view of the above problems, and it is an object of the present invention to provide an injection volume regulating device for a liquid medicine, which enables constant and continuous administration of the liquid medicine such as Ringers solution or a special medicine for injection together with precise regulation of an injection volume of the liquid medicine, can fix a packing for sealing in place while preventing the packing from infiltrating a passage.

It is another object of the present invention to provide an injection volume regulating device for a liquid medicine, which comprises a body gripped with one hand, and a regulating member equipped to the body to be rotated by the thumb with the body gripped in the hand, so that the injection volume of the liquid medicine can be easily regulated with one hand.

It is yet another object of the present invention to provide an injection volume regulating device for a liquid medicine, which enables a predetermined injection volume of the liquid medicine to be reliably set at any position when regulating the injection volume of the liquid medicine.

Technical Solution

In accordance with an aspect of the present invention, the above and other objects can be accomplished by the provision of an injection volume regulating device for a liquid medicine, the device being equipped to a hose hermetically connected to a lower end of a pack containing the liquid medicine and to a needle, comprising: a disk-shaped fixing member comprising an inlet connected to the hose to be supplied with the liquid medicine from the pack through the hose, an inflow hole connected to the inlet to deliver the liquid medicine to a passage recess of a regulating member, an outflow hole to be supplied with the liquid medicine from a liquid medicine-delivering groove of the regulating member, an outlet connected to the outflow hole to discharge the liquid medicine to the hose so as to allow the liquid medicine to be supplied to the needle, and an insertion hole to be equipped with the fastening member; the regulating member having a disk shape, and comprising the passage recess having an arcuate shape and being connected to the inflow hole to be supplied with the liquid medicine from the inflow hole, the liquid medicine-delivering groove formed at one end of the passage recess and connected to the outflow hole, and an insertion hole to be equipped with the fastening member; a passage recess-sealing member sealing the passage recess while communicating the inflow hole with the passage recess, and an outflow hole-sealing member sealing the outflow hole; and a fastening member passing through the insertion holes of the fixing member and the regulating member to fasten the fixing member to the regulating member.

The device may further comprise a handle detachably equipped to a lower portion of the fixing member such that the handle can be gripped with one hand.

In accordance with another aspect of the present invention, an injection volume regulating device for a liquid medicine, equipped to a hose air-tightly connected to a lower end of a pack containing a liquid medicine and to a needle, comprises: a first fixing member comprising an inlet connected to the hose to be supplied with the liquid medicine from the pack through the hose, an inflow hole connected to the inlet to deliver the liquid medicine to a passage recess of a regulating member, an outflow hole to be supplied with the liquid medicine from a liquid medicine-delivering groove of the regulating member, an outlet connected to the outflow hole to discharge the liquid medicine to the hose so as to allow the liquid medicine to be supplied to the needle, and a first fastening member; the regulating member having a disk shape, and comprising the passage recess having an arcuate shape and being connected to the inflow hole to be supplied with the liquid medicine from the inflow hole, the liquid medicine-delivering groove formed at one end of the passage recess and connected to the outflow hole, and an insertion hole to be equipped with the fastening member; a passage recess-sealing member sealing the passage recess and having a through-hole connecting the inflow hole and the passage recess, and an outflow hole-sealing member sealing the outflow hole; and a second fixing member having a second fastening member passing through the insertion hole of the regulating member to be fastened to the first fastening member.

The first and second fixing members may be fastened to each other to constitute an elongated casing to be gripped with one hand while allowing a portion of the regulating member to be exposed through the casing.

The passage recess may have a cross-sectional area gradually decreased in a direction away from the liquid medicine-delivering groove.

The regulating member may further comprise one or more in-recess protrusions having a greater central angle than that of the passage recess, and being separated a predetermined distance from the passage recess.

The regulating member may further comprise an outflow hole-sealing member protrusion to compress the outflow hole-sealing member.

The passage recess-sealing member may be formed with several protrusions, and the fixing member or the first fixing member may be formed with sites on which the protrusions are seated.

The regulating member may be rotated within a predetermined range defined by a stopper formed on an outer peripheral surface of the fixing member and a latching piece formed on an outer peripheral surface of the regulating member.

The fastening member may further comprise a male fastening member having a hook formed thereon, and a female fastening member having a hook receiving hole to seat the hook, and a hook insertion hole through which the hook is inserted.

The fastening member may further comprise a fixing pin passing through the center of the male fastening member and the female fastening member and being inserted into the hook while fastening the male fastening member to the female fastening member.

The device may further comprise a locking mechanism to lock the regulating member at a predetermined location.

The locking mechanism may comprise a cylindrical spline formed on the fastening member towards the regulating member, and a fixing bolt passing through a fixing bolt hole formed in a side surface of the regulating member to engage with the spline and restrict rotation of the regulating member.

The locking mechanism may comprise a ring-shaped spline protruded from a surface facing a female fastening member of a regulating member, and a fixing bolt passing through a fixing bolt hole formed in the female fastening member to engage with the spline and restrict rotation of the regulating member.

In the locking mechanism, the fixing bolt hole may have threads formed thereon, and the fixing bolt may comprise a screw having a sharp end and threads to engage with the fixing bolt hole, and a head having a wrench groove formed thereon to allow a wrench to be inserted and rotated.

The locking mechanism may further comprise a spring equipped around the fixing bolt hole and having a protrusion contacting an end of the fixing bolt to be engaged with or disengaged from the spline, the fixing bolt hole may have threads formed thereon, and the fixing bolt may comprise a screw having threads formed thereon to engage with the fixing bolt hole, and a wrench groove adapted to receive a wrench when rotating the fixing bolt, the screw having a flat end.

Advantageous Effects

As apparent from the above description, the present invention provides an injection volume regulating device for a liquid medicine supplied from an injection device for the liquid medicine such as Ringers solution and a special liquid medicine for injection according to length and width of a passage, thereby enabling a precisely regulated amount of the liquid medicine to be administered in required amount to a patient requiring constant and continuous administration of the liquid medicine, and preventing excessive administration of the liquid medicine, which frequently occurs due to deformation in a conventional injection volume regulating device for the liquid medicine. In addition, the injection volume regulating device can be manufactured with lower cost than an injector.

Additionally, the present invention can solve the problems of the conventional injection volume regulating device for the liquid medicine in which a rubber packing compresses a passage and interferes with flow of the liquid medicine, in which a fastening member is pushed by restoring force of the rubber packing, and in which the rubber packing is not fixed in the device.

According to the present invention, the device can be easily operated with one hand, thereby enhancing operating efficiency.

According to the present invention, the device has a regulating member restricted in movement at a predetermined location, thereby enabling an exact amount of liquid medicine to be reliably administered to a patient.

Specifically, a wrench groove is formed on a head of a fixing bolt which is a component of a locking mechanism for fixing the regulating member at the pre-determined location, so that the regulating member can be released from a fixed state by any one even with a wrench unsuitable for the wrench groove.

BRIEF DESCRIPTION OF THE DRAWINGS

The above and other objects, features and other advantages of the present invention will be more clearly understood from the following detailed description taken in conjunction with the accompanying drawings, in which:

FIG. 1 is an exploded perspective view illustrating components of an injection volume regulating device for a liquid medicine in accordance with a first embodiment of the present invention;

FIG. 2 is a plan view illustrating the components of the device in accordance with the first embodiment of the invention;

FIG. 3 is a plan view illustrating a fixing member of the device in accordance with the first embodiment of the invention;

FIG. 4 is a front view illustrating the fixing member of the device in accordance with the first embodiment of the invention;

FIG. 5 is a plan view illustrating a regulating member of the device in accordance with the first embodiment of the invention;

FIG. 6 is a partially cutaway perspective view illustrating the regulating member of the device in accordance with the first embodiment of the invention;

FIG. 7 is a front view illustrating the regulating member of the device in accordance with the first embodiment of the invention;

FIG. 8 is a perspective view illustrating the device in an assembled stated in accordance with the first embodiment of the invention;

FIG. 9 is a view illustrating the device applied to a hose in accordance with the first embodiment of the invention;

FIG. 10 is a first explanatory view illustrating operation of the device in accordance with the first embodiment of the invention;

FIG. 11 is a second explanatory view illustrating operation of the device in accordance with the first embodiment of the invention;

FIG. 12 is a third explanatory view illustrating operation of the device in accordance with the first embodiment of the invention;

FIG. 13 is an exploded perspective view illustrating components of an injection volume regulating device for a liquid medicine in accordance with a second embodiment of the present invention;

FIG. 14 is a perspective view illustrating the device in an assembled stated in accordance with the second embodiment of the invention;

FIG. 15 is an exploded perspective view illustrating components of an injection volume regulating device for a liquid medicine in accordance with a third embodiment of the present invention;

FIG. 16 is a perspective view illustrating the device in an assembled stated in accordance with the third embodiment of the invention;

FIG. 17 is an exploded perspective view illustrating components of an injection volume regulating device for a liquid medicine in accordance with a fourth embodiment of the present invention;

FIG. 18 is a perspective view illustrating a regulating member and a female fastening member of the device in accordance with the fourth embodiment of the invention;

FIG. 19 is an exploded perspective view illustrating components of an injection volume regulating device for a liquid medicine in accordance with a fifth embodiment of the present invention;

FIG. 20 is a plan view illustrating the components of the device in accordance with the fifth embodiment of the invention;

FIG. 21 is a perspective view illustrating a regulating member and a female fastening member of the device in accordance with the fifth embodiment of the invention when being seen from an upper portion; and FIG. 22 is a perspective view illustrating the regulating member and the female fastening member of the device in accordance with the fifth embodiment of the invention when being seen from a lower portion.

BEST MODE FOR CARRYING OUT THE INVENTION

Embodiments of the present invention will be described with reference to the drawings as follows.

FIG. 1 is an exploded perspective view illustrating components of an injection volume regulating device in accordance with a first embodiment of the present invention. In FIG. 1, the injection volume regulating device of the first embodiment comprises a fixing member 12 to which a passage recess-sealing member 13 and an outflow hole-sealing member 14 are fixed, a regulating member 15 brought into contact with the fixing member 12, a male fastening member 11 having a hook 112 formed thereon, a female fastening member 16 having a hook insertion tube 161 formed thereon such that the hook 112 is inserted into the hook insertion tube 161, and a fixing pin 17 inserted and fixed to a hole formed between the hook 112 and the hook insertion tube 161 when the male fastening member 11 is coupled to the female fastening member 16 through insertion holes 129 and 157 respectively formed through the fixing member 12 and the regulating member 15.

The male fastening member 11 comprises a fastening member base 110, a fixing piece 11, and a fixing pin-receiving hole 113 in addition to the hook 112.

The fastening member base 110 has a disk shape, and is fitted to a rear side of the fixing member 12. The fixing piece 111 is formed on one side of the fastening member base 110 to latch to protrusions on the rear side of the fixing member 12 so as to prevent the male fastening member 11 from rotating.

The hook 12 is formed at the center of the fastening member base 110. Although the hook is illustrated as having two legs in the first embodiment, the hook may have four or more legs.

The fixing pin-receiving hole 113 is formed at the center of the fastening member base 110, and is coaxial with the center of the hook 112.

The female fastening member 16 is fastened to the male fastening member 11. The female fastening member 16 comprises a fastening member base 160 and a fixing pin-receiving hole 164 in addition to the hook insertion tube 161. The hook insertion tube 161 is formed with a hook insertion hole 162 and a hook seating hole 163.

The fastening member base 160 has a disk shape, and is equipped to a rear side of the regulating member 15.

The hook insertion tube 161 is formed at the center of the fastening member base 160, and the fixing pin-receiving hole 164 is formed at the center of the fastening member base 160 so as to be coaxial with the center of the hook insertion tube 161.

The hook insertion tube 161 has the hook insertion hole 162 which allows the two legs of the hook 112 to be narrowed inward and inserted therethrough, and the hook seating hole 163 which allows the two legs of the hook 112 to be widened and seated therein as the hook further advances in the hook insertion tube 161.

The passage recess-sealing member 13 has a ring shape, and is formed of a rubber material. The passage recess-sealing member 13 has horizontal protrusions 135 and 136 formed on a horizontal plane of a ring base 130, and vertical protrusions 132, 133 and 134 vertical to the horizontal plane in order to prevent the passage recess-sealing member 13 from rotating when being seated on the fixing member 12.

In addition, the passage recess-sealing member 13 has a through-hole 131 serving to communicate an inflow hole 123 with a passage recess 153 of the fixing member 12.

The outflow hole-sealing member 14 has a smaller ring shape than that of the passage recess-sealing member 13, and is formed of the rubber material. The outflow hole-sealing member 14 is mounted on a mounting groove 125 formed on an inner surface of the fixing member 12.

The fixing pin 17 has a first profile 171, and a second profile 172 having a different cross-section from that of the first profile 171. This shape is provided for the purpose of forcing the fixing pin 17 to be inserted only in one direction. In this regard, the fixing pin-receiving holes 113 and 164 of the fastening members 11 and 16 have an elliptical shape and a circular shape corresponding to the first and second profiles 171 and 172 of the fixing pin 17, respectively. The first profile 171 has a greater cross-sectional area than the second profile 172.

As a result, when press-fitting the fixing pin 17 from the male fastening member 11 to the female fastening member 16 by striking a head of the fixing pin 17, the fixing pin 17 cannot advance beyond a predetermined distance due to variation in cross-sectional areas of the first and second profiles 171 and 172 of the fixing pin 17.

In addition, preferably, the fixing pin 17 is slightly tapered for press-fitting.

As the fixing pin 17 is inserted through the fixing pin-receiving holes 113 and 164 with the male fastening member 11 fastened to the female fastening member 16, a gap between the legs of the hook 112 can be maintained constant, so that the male fastening member 11 and the female fastening member 16 are prevented from being separated due to restoration force of the passage recess-sealing member 13 and the outflow hole-sealing member 14, thereby enhancing precision of the product.

The fixing member 12 has an inlet 121 and an outlet 122 for the liquid medicine. The fixing member 12 is formed with a stopper 127 to which a latching piece 151 of the regulating member 15 is latched to define an initial location and a final location of the regulating member 15.

FIG. 2 is a plan view illustrating the components shown in FIG. 1 and arranged in an order of assembling the components, in which the male fastening member 11 having the hook 112 formed thereon is shown.

Although not shown in FIG. 2, the fixing pin-receiving holes 113 and 164 are shown in FIG. 2 as being formed in the male fastening member 11 and female fastening member 16, respectively.

FIGS. 3 and 4 are a plan view and a front view illustrating the fixing member 12.

The fixing member 12 has a disk shape, and has a rounded shape formed on an outer surface thereof so as to be easily gripped with hand.

In the fixing member 12, the inlet 121 is supplied with the liquid medicine from a pack 20, and the outlet 122 allows the liquid medicine to be supplied to a needle 22 therethrough. The inlet 121 and the outlet 122 are formed coplanar and inline with each other on the fixing member 12.

The fixing member 12 has a seat formed on a surface brought into contact with the regulating member 15 to mount the passage recess-sealing member 13, an outflow hole 126 inside the seat, and an outflow hole-sealing member mounting groove 125 inside the outflow hole 126 to mount the outflow hole-sealing member 14, in which the seat, the outflow hole 126, and the mounting groove 125 are formed as concentric circles on the fixing member 12, respectively, and in which the inflow hole 123 communicated with the inlet 121 is matched to the through-hole 131 of the passage recess-sealing member 13.

The horizontal protrusions 135 and 136 are located on horizontal protrusion sites 1244 and 1245, and the vertical protrusions 132, 133 and 134 are located on vertical protrusion sites 1241, 1242 and 1243, respectively.

The stopper 127 is formed at a lower portion of the inlet 121 of the fixing member 12 to latch to the latching piece 151 of the regulating member 15.

As shown in FIG. 4, the inlet 121 is communicated with the inflow hole 123 through a liquid medicine inflow pipe 1211, and the outflow hole 126 is communicated with the outlet 122 through a liquid medicine discharge pipe 1221.

FIGS. 5 to 7 are a plan view, a partially cutaway perspective view, and a cross-sectional view of the regulating member 15 in the device according to the first embodiment.

As shown in FIG. 5, the regulating member 15 has a substantially disk shape, and is formed with the latching piece 151, the passage recess 153, an in-recess protrusion 154, a protrusion 155, an outflow hole-sealing member protrusion 156, and the insertion hole 157. The regulating member 15 has a rounded outer peripheral surface to allow the regulating member 15 to be easily gripped.

The latching piece 151 is located corresponding to the stopper 127 of the fixing member 12 such that the initial location of the latching piece 151 is at the left side of the stopper 127 located in line A-A of FIG. 5, and the final location of the locating piece 151 is at the right side of the stopper 127.

The passage recess 153 has an arcuate shape, the central angle of which is in the range of 330~350 degrees.

As shown in FIG. 6, the passage recess 153 has a substantially rectangular cross section, and a cross-sectional area gradually decreased in a direction away from a liquid medicine-delivering groove 1531.

Variation in the cross-sectional area of the passage recess 153 is obtained by changing a width or a depth thereof.

The passage recess 153 is formed on the regulating member 15 such that the passage recess is separated from the central axis of the regulating member 151 at the same distance as that of the inflow hole 123 of the fixing member 12. Thus, even if the regulating member 15 is rotated, the passage recess 153 is connected to the inflow hole 123.

As a matter of course, the through-hole 131 of the passage recess-sealing member 13 is located between the passage recess 153 and the inflow hole 123 to communicate the passage recess 153 with the inflow hole 123.

The in-recess protrusion 154 is formed outside the passage recess 153.

The in-recess protrusion 154 is formed to prevent the passage recess-sealing member 13 formed of a flexible material such as rubber from being pushed into the passage recess 153 and then narrowing or blocking the passage recess 153 due to deformation caused by compressing force of the fastening member when sealing the passage recess 153 except for the inflow hole 123 with the passage recess-sealing member 13.

That is, the in-recess protrusion 154 serves to deform the passage recess-sealing member 13 in an opposite direction to the passage recess 153, thereby preventing the passage recess-sealing member 13 from being deformed inside the in-recess protrusion 154.

Accordingly, the in-recess protrusion 154 has a central angle greater than or equal to that of the passage recess 153.

Meanwhile, although one in-recess protrusion 154 is provided in the first embodiment, it is desirable to form two or more in-recess protrusions 154 on the regulating member 15 in order to more securely prevent the passage recess-sealing member 13 from being deformed inside the in-recess protrusion 154.

In the case of two in-recess protrusions 154, when they are located on inner and outer peripheral surfaces of the passage recess 153, respectively, it is easy to prevent the passage recess-sealing member 13 from being deformed inside the in-recess protrusion 154.

The in-recess protrusion 154 preferably has a circular shape rather than the arcuate shape to support the passage recess-sealing member 13.

The liquid medicine-delivering groove 1531 formed at one end of the passage recess 153 serves to deliver the liquid medicine having flown through the passage recess 153 to the outflow hole 126 of the fixing member 12.

Thus, the liquid medicine-delivering groove 1531 is formed downward perpendicular to the passage recess 153.

The protrusion 155 is formed higher than the surface of the passage recess 153 inside the liquid medicine-delivering groove 1531. The protrusion 155 serves to push the outflow hole-sealing member 14 mounted on the mounting groove 125.

Additionally, the protrusion 155 is formed with the outflow hole-sealing member protrusion 156 to ensure sealing of the outflow hole-sealing member 14.

In FIGS. 6 and 7, positional relationship between the passage recess 153, the in-recess protrusion 154, the protrusion 155, and the outflow hole-sealing member protrusion 156 is clearly shown.

FIG. 8 is a perspective view illustrating the device in an assembled state according to the first embodiment.

In the assembled device, since the fixing member 12 and the regulating member 15 are fixed by the male fastening member 11 and the female fastening member 16 after being sealed by the passage recess-sealing member 13 and the outflow hole-sealing member 14, and the male fastening member 11 is fixed to the fixing member 12 by the fixing piece 111, only the regulating member 15 can be rotated.

With the regulating member 15 positioned at the initial location, an indicating mark is made on the device in an upper direction, and then notches are made on an outer peripheral surface of the female fastening member 16, thereby allowing an injection rate of the liquid medicine regulated by means of the regulating device according to a rotational degree of the regulating member 15 to be easily recognized.

If the liquid medicine has a high viscosity, the fluidity of the liquid medicine is lowered. Thus, the regulating member 15 must be more widely opened than a conventional liquid medicine in order to allow the liquid medicine to flow smoothly.

For this purpose, an opening degree of the regulating device can be controlled by rotating the regulating member 15 according to the viscosity of the liquid medicine with reference to the notches. It is more preferable to form a number of notches corresponding to viscosities of liquid medicines.

FIG. 9 is a view illustrating the device according to the first embodiment connected to the pack 20 containing a liquid medicine and to the needle 22.

At this time, a distance between the pack 20 and the injection volume regulating device 10 for the liquid medicine, and a distance between the injection volume regulating device 10 and the needle 20 can be changed according to patients.

In other words, when using the regulating device for an infant patient, it is desirable that a distance between the injection volume regulating device 10 and the needle 22 is extended in order to prevent the infant from touching the injection volume regulating device 10, and when using a migratory rack with the regulating device, it is desirable that a distance between the injection volume regulating device 10 and the needle 22 is shortened to prevent a liquid medicine pipe from being swung by the injection volume regulating device 10.

Operation of the injection volume regulating device 10 according to the first embodiment will be described.

A liquid medicine flows in sequence of; inlet 121→liquid medicine inflow pipe 1211→inflow hole 123→through-hole 131→passage recess 153→liquid medicine-delivering groove 1531→outflow hole 126→liquid medicine discharge pipe 1221→outlet 122.

As a result, regulation for an injection amount of the liquid medicine can be achieved by changing a flowing length of the liquid medicine flowing along the passage recess 153.

As described above, the passage recess 153 is decreased in cross-sectional area in the direction away from the liquid medicine-delivering groove 1531. As a result, the amount of the liquid medicine delivered from the inflow hole 123 to the passage recess 153 is decreased in the direction away from the liquid medicine-delivering groove 1531, and is increased in a direction towards the liquid medicine-delivering groove 1531, so that supply of the liquid medicine can be regulated.

As shown in FIG. 10, when the regulating member 15 is positioned at an initial location, since the liquid medicine directly flows from the inflow hole 123 to the outflow hole 126 through the liquid medicine-delivering groove 1531 substantially without passing through the passage recess 153, an outflow amount of the liquid medicine through the outlet 122 is maximized.

As shown in FIG. 11, when the regulating member 15 is operated to allow the inflow hole 123 to be positioned at a final location, since the liquid medicine flows out through a portion of the passage recess 153 having a minimum cross-sectional area, an outflow amount of the liquid medicine through the outlet 122 is minimized.

As shown in FIG. 12, when the regulating member 15 is operated to prevent the inflow hole 123 from being located at the passage recess 153, since the passage recess 153 is blocked by the passage recess-sealing member 13, the liquid medicine does not flow through the outlet 122.

When operating the regulating device 15 according to the first embodiment, the regulating member 15 can be regulated by the thumb with the device gripped in only one hand.

However, since the regulating member 15 has the same size as that of the fixing member 12, it may be difficult to rotate the passage recess 153, and it may be inconvenient to grip the device.

Modifications of the first embodiment are shown as a second embodiment in FIGS. 13 and 14, and as a third embodiment in FIGS. 15 and 16.

FIG. 13 is an exploded perspective view illustrating components of an injection volume regulating device according to a second embodiment, and FIG. 14 is a perspective view illustrating the assembled device of the second embodiment.

Most components of the device according to the second embodiment are the same as those of the device according to the first embodiment, except that the device of the second embodiment comprises a fixing member 18 having a smooth outer peripheral surface instead of the fixing member 12 having a rounded outer peripheral surface, and a handle 19 detachably mounted to the fixing member 18.

Thus, the device of the second embodiment has an advantage in that since an injection volume of the liquid medicine can be regulated by rotating a rounded peripheral outer surface 152 of a regulating member 15 using a finger in a state of the handle 19 being gripped in the hand, the injection volume regulating device of the second embodiment further enhances the user convenience in comparison to the first embodiment.

In addition, when the handle 19 is separated from the fixing member 18, arbitrary operation of the regulating member 15 can be inhibited, which enables prevention of arbitrary regulation of the injection amount of the liquid medicine by the patient, and results in stable injection of the liquid medicine.

FIG. 15 is an exploded perspective view illustrating components of an injection volume regulating device according to the third embodiment, and FIG. 16 is a perspective view illustrating the assembled device of the third embodiment.

According to the third embodiment, the injection volume regulating device comprises a first fixing member 31 constructed by coupling the fixing member 12 and the male fastening member 11 of the injection volume regulating device according to the first embodiment, and a second fixing member 33 corresponding to the female fastening member 16 of the injection volume regulating device according to the first embodiment so that, when the first fixing member 31 is coupled with the second fixing member 33, the first and second fixing members 31 and 33 constitute an easily-gripped elongated casing.

In addition, a regulating member 32, a passage recess-sealing member 34 and an outflow hole-sealing member 35 corresponding to the regulating member 15, the passage recess-sealing member 13 and the outflow hole-sealing member 14 of the first embodiment are disposed between the first and second fixing members 31 and 33.

The regulating member 32 is slightly protruded from the casing such that the regulating member 32 can be rotated by hand. Furthermore, according to the second embodiment, since an indicating mark is made on a side surface of the regulating member 32, it is possible to precisely regulate an amount of the liquid medicine according to a rotated degree of the regulating member 32. Alternatively, for the same purpose, an indicating mark can be formed on a flat surface of the regulating member 32 with an indicating window 332 provided on the second fixing member 33.

The first fixing member 31 is formed with an inlet 311 and an outlet 312 for the liquid medicine.

Reference numeral 331 indicates a hook insertion pipe provided to the second fixing member 33. As with the first embodiment, a hook (not shown) is provided to the first fixing member 31.

Other components of the injection volume regulating device according to the third embodiment are the same as those of the injection volume regulating device according to the first embodiment.

With this construction, the injection volume regulating device of the third embodiment is more easily gripped with one hand than the first embodiment, thereby further enhancing user convenience.

FIGS. 17 to 22 are views illustrating injection volume regulating devices for a liquid medicine according to fourth and fifth embodiments, in which each of the devices further comprises a locking mechanism to forcibly stop a regulating member at any location, thereby enhancing product reliability.

FIGS. 17 and 18 show the injection volume regulating device according to the fourth embodiment, in which the locking mechanism comprises a cylindrical spline 54 formed on a fastening member 50 towards a regulating member 40, and a fixing bolt 44 passing through a fixing bolt hole 42 formed on a side surface of the regulating member 40 to engage with the spline 54 and restrict rotation of the regulating member 40.

Meanwhile, other constructions of the regulating member 40 and the female fastening member 50 of the injection volume regulating device according to the fourth embodiment are the same as those of the first embodiment.

The height of the spline 54 is designed so as not to interfere with an inner surface of the regulating member 40.

The spline 54 must have a diameter smaller than that of a fastening member plate 55 but greater than that of the hook insertion tube 51.

The spline 54 has a substantially spur gear shape, each thread of which preferably has a triangular cross section in order to allow easy engagement with the fixing bolt 44.

One end of the fixing bolt 44 brought into contact with the spline 54 has a pointed shape such that the end of the fixing bolt 44 is engaged with the spline 54 and fixes the regulating member 40.

Additionally, the fixing bolt 44 comprises a screw 47, and a fixing bolt head 46 which has a wrench groove 45 formed thereon.

As a matter of course, although not shown in the drawings, the fixing bolt hole 42 is formed with female threads which engage with the screw 47 formed on the fixing bolt 44.

Accordingly, in order to lock the regulating member 40, the wrench (not shown) is fastened to the wrench groove 45 of the fixing bolt head 46, and is rotated, such that the pointed end of the fixing bolt 44 advances towards the spline 54 until the fixing bolt 44 is finally screwed into a groove of the spline 54.

On the contrary, in order to unlock the regulating member 40, the wrench (not shown) is fastened to the wrench groove 45 of the fixing bolt head 46, and is rotated, such that the pointed end of the fixing bolt 44 is withdrawn from the spline 54 until the fixing bolt 44 is separated from the groove of the spline 54.

FIGS. 19 to 22 show the injection volume regulating device according to the fifth embodiment, in which the locking mechanism comprises a ring-shaped spline 64 protruded from a surface facing a female fastening member 16 of a regulating member 60, and a fixing bolt 76 passing through a fixing bolt hole 81 formed in the female fastening member 70 to engage with the spline 64 and restrict rotation of the regulating member 60.

Other constructions of the regulating member 60 and the female fastening member 70 of the injection volume regulating device of the fifth embodiment are the same as those of the first embodiment.

The height of the spline 64 is designed so as not to interfere with the female fastening member 70.

Preferably, the spline 64 has a wide area advantageous for contact with the fixing bolt 76.

The spline 64 has a substantially bevel gear shape with an approximate cone angle of 0, in which a thread of the gear has a triangular cross section in order to allow easy engagement with the fixing bolt 76.

One end of the fixing bolt 76 brought into contact with the spline 64 has a flat shape.

Additionally, the fixing bolt 76 comprises a screw 80, and a fixing bolt head 79 which has a wrench groove 78 formed thereon.

As a matter of course, although not shown in the drawings, a fixing bolt hole 81 is formed with female threads which can engage with the screw 80 formed on the fixing bolt 76.

Moreover, the locking mechanism further comprises a plate spring 75 equipped around the fixing bolt hole 81 and having a protrusion which can be engaged with or disengaged from the spline 64.

Accordingly, in order to lock the regulating member 60, the wrench (not shown) is fastened to the wrench groove 78 of the fixing bolt head 79, and is rotated thereon, such that the end of the fixing bolt 96 pushes the plate spring 75 to allow the protrusion of the plate spring 75 to advance towards the spline 54 until the fixing bolt 96 is screwed into a groove of the spline 64.

On the contrary, in order to unlock the regulating member 60, the wrench (not shown) is fastened to the wrench groove 78 of the fixing bolt head 79, and is rotated thereon, such that the sharp end of the fixing bolt 79 is withdrawn from the spline 64 while the plate spring 75 moves in a direction opposite to the spline 64 by its restoring force until the fixing bolt 79 to allow the protrusion of the plate spring 75 to be withdrawn from the spline 64 until the fixing bolt 79 is separated from the groove of the spline 54.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention can be applied to a valve for controlling flux in general industries as well as to the medical industry.

The invention claimed is:

1. An injection volume regulating device for a liquid medicine, the device being equipped between a first hose and a second hose, the first hose being hermetically connected to a lower end of a pack containing the liquid medicine and the second hose being connected to a needle, and comprising:
 a disk-shaped fixing member comprising an inlet connected to the first hose to be supplied with the liquid medicine from the pack through the first hose, an inflow hole connected to the inlet to deliver the liquid medicine to a passage recess of a regulating member, an outflow hole to be supplied with the liquid medicine from a liquid medicine-delivering groove of the regulating member, an outlet connected to the outflow hole to discharge the liquid medicine to the second hose so as to allow the liquid medicine to be supplied to the needle, and an insertion hole to be equipped with a fastening member;
 the regulating member having a disk shape, and comprising the passage recess having an arcuate shape and being connected to the inflow hole to be supplied with the liquid medicine from the inflow hole, the liquid medicine-delivering groove formed at one end of the passage recess and connected to the outflow hole, and an insertion hole to be equipped with the fastening member;

a passage recess-sealing member sealing the passage recess while communicating the inflow hole with the passage recess, and an outflow hole-sealing member sealing the outflow hole; and the fastening member passing through the insertion hole of the fixing member and the regulating member to fasten the fixing member to the regulating member, and a handle detachably equipped to a lower portion of the fixing member such that the handle can be gripped with one hand, wherein the regulating member further comprises one or more in-recess protrusions having a greater central angle than that of the passage recess and being separated a predetermined distance from the passage recess.

2. The device according to claim 1, wherein the passage recess has a cross-sectional area gradually decreased in a direction away from the liquid medicine-delivering groove.

3. The device according to claim 1, wherein the regulating member further comprises an outflow hole-sealing member protrusion to compress the outflow hole-sealing member.

4. The device according to claim 1, wherein the passage recess-sealing member is formed with several protrusions, and the fixing member is formed with sites on which the protrusions are seated.

5. The device according to claim 1, wherein the regulating member is rotated within a range defined by a stopper formed on an outer peripheral surface of the fixing member and a latching piece formed on an outer peripheral surface of the regulating member.

6. The device according to claim 1, wherein the fastening member further comprises a male fastening member having a hook formed thereon, and a female fastening member having a hook receiving hole to seat the hook, and a hook insertion hole through which the hook is inserted.

7. The device according to claim 6, wherein the fastening member further comprises a fixing pin passing through the center of the male fastening member and the female fastening member and being inserted inside the hook while fastening the male fastening member to the female fastening member.

8. The device according to claim 1, further comprising: a locking mechanism to lock the regulating member at a predetermined location.

9. The device according to claim 8, wherein the locking mechanism comprises a cylindrical spline formed on the fastening member towards the regulating member, and a fixing bolt passing through a fixing bolt hole formed in a side surface of the regulating member to engage with the spline and restrict rotation of the regulating member.

10. The device according to claim 8, wherein the locking mechanism comprises a ring-shaped spline protruded from a surface facing the fastening member of the regulating member, and a fixing bolt passing through a fixing bolt hole formed in the fastening member to engage with the spline and restrict rotation of the regulating member.

11. The device according to one of claim 9 or claim 10, wherein the fixing bolt hole has threads formed thereon, and the fixing bolt comprises a screw having a sharp end and threads to engage with the fixing bolt hole, and a head having a wrench groove formed thereon to allow a wrench to be inserted and rotated.

12. The device according to one of claim 9 or claim 10, wherein the locking mechanism further comprises a spring equipped around the fixing bolt hole and having a protrusion contacting an end of the fixing bolt to be engaged with or disengaged from the spline, wherein the fixing bolt hole has threads formed thereon, and wherein the fixing bolt comprises a screw having a flat end and threads to engage with the fixing bolt hole, and a head having a wrench groove formed thereon to allow a wrench to be inserted and rotated.

13. An injection volume regulating device for a liquid medicine, the device being equipped between a first hose and a second hose, the first hose being hermetically connected to a lower end of a pack containing the liquid medicine and the second hose being connected to a needle, and comprising:

a disk-shaped fixing member comprising an inlet connected to the first hose to be supplied with the liquid medicine from the pack through the first hose, an inflow hole connected to the inlet to deliver the liquid medicine to a passage recess of a regulating member, an outflow hole to be supplied with the liquid medicine from a liquid medicine-delivering groove of the regulating member, an outlet connected to the outflow hole to discharge the liquid medicine to the second hose so as to allow the liquid medicine to be supplied to the needle, and an insertion hole to be equipped with a fastening member;

the regulating member having a disk shape, and comprising the passage recess having an arcuate shape and being connected to the inflow hole to be supplied with the liquid medicine from the inflow hole, the liquid medicine-delivering groove formed at one end of the passage recess and connected to the outflow hole, and an insertion hole to be equipped with the fastening member;

a passage recess-sealing member sealing the passage recess while communicating the inflow hole with the passage recess, and an outflow hole-sealing member sealing the outflow hole; and the fastening member passing through the insertion hole of the fixing member and the regulating member to fasten the fixing member to the regulating member, wherein the regulating member further comprises one or more in-recess protrusions having a greater central angle than that of the passage recess and being separated a predetermined distance from the passage recess; and wherein the regulating member is rotated within a range defined by a stopper formed on an outer peripheral surface of the fixing member and a latching piece formed on an outer peripheral surface of the regulating member.

14. The device according to claim 13, wherein the passage recess has a cross-sectional area gradually decreased in a direction away from the liquid medicine-delivering groove.

15. The device according to claim 13, wherein the passage recess-sealing member is formed with several protrusions, and the fixing member is formed with sites on which the protrusions are seated.

16. The device according to claim 13, wherein the regulating member is rotated within a range defined by a stopper formed on an outer peripheral surface of the fixing member and a latching piece formed on an outer peripheral surface of the regulating member.

17. The device according to claim 13, wherein the fastening member further comprises a male fastening member having a hook formed thereon, and a female fastening member having a hook receiving hole to seat the hook, and a hook insertion hole through which the hook is inserted.

18. The device according to claim 13, further comprising: a locking mechanism to lock the regulating member at a predetermined location.

* * * * *